United States Patent [19]

Zaiger et al.

[11] Patent Number: Plant 5,287

[45] Date of Patent: Oct. 2, 1984

[54] PLUM TREE '42-GA-252'

[76] Inventors: Chris F. Zaiger, 537 Rosemore Ave.; Gary N. Zaiger, 1907 Elm Ave.; Leigh M. Gardner, 1207 Grimes Ave.; Grant G. Zaiger, 2121 Elm Ave., all of Modesto, Calif. 95351

[21] Appl. No.: 465,529

[22] Filed: Feb. 11, 1983

[51] Int. Cl.[3] ..... A01H 5/00

[52] U.S. Cl. ..... Plt./38

[58] Field of Search ..... Plt./38

*Primary Examiner*—James R. Feyrer

*Attorney, Agent, or Firm*—Roger B. Webster

[57] ABSTRACT

A new and distinct variety of plum tree which is of medium to large size, vigorous, upright, medium dense, and vase form; foliated with large, smooth, many oblanceolate but some elliptical leaves having globose glands and a serrate margin; blooms from medium size, plump buds; the flowers being white and of medium size; and is a regular and productive bearer of medium size, somewhat oblate, clingstone fruit having red skin, firm, yellow flesh, and a brownish-orange stone.

1 Drawing Figure

BACKGROUD OF THE VARIETY

1. Field of the Invention

In the field of plant genetics we conduct an extensive and continuing plant breeding program including the origination and asexual reproduction of orchard trees, and of which peaches, apricots, and plums are exemplary. It was against this background of our activities that the present variety of plum tree was originated and asexually reproduced by us in an experimental orchard located at Modesto, Stanislaus County, Calif.

2. Classification of the Variety

The present new and distinct variety of plum tree is embraced by Class 38, Plants, of the U.S. Patent Office Manual of Classification.

3. Prior Varieties

Among the existent varieties of plum trees which are known to us, and mentioned herein, are Spring Beaut (U.S. Plant Pat. No. 4,394) and Nubiana (unpatented).

ORIGIN OF THE VARIETY

The present variety of plum tree was originated by us, in the aforesaid experimental orchard, as a selection from a large number of seedlings resulting from a cross between Spring Beaut and Nubiana. Such seedlings were planted and grown under careful and continuing observation, and one such seedling—which is the present variety—evidenced, in maturity, especially novel and desirable characteristics, and hence—because of its commercial potential—was selected for asexual reproduction.

ASEXUAL REPRODUCTION OF THE VARIETY

The present variety of plum tree was asexually reproduced, in the aforesaid experimental orchard, by budding, and such reproductions ran true to the original tree and its fruit in all respects.

SUMMARY OF THE VARIETY

The present variety of plum tree is, characteristically, of medium to large size, vigorous, upright, medium dense, and vase form; foliated with large, smooth, many oblanceolate but some elliptical leaves having globose glands and a serrate margin; blooms from medium size, plump buds; the flowers being white and of medium size; and is a regular and productive bearer of medium size, somewhat oblate, clingstone fruit having red skin, firm, yellow flesh, and a brownish-orange stone.

The present variety of plum tree is further, and more particularly, characterized by evenly distributed, uniform fruit which—while having the general oblate shape of the Nubiana—is in harvest three days earlier than the Spring Beaut; the fruit having good keeping, long distance shipping, and eating qualities.

BRIEF DESCRIPTION OF THE DRAWING

The drawing comprises illustrations, by photographic reproduction in color, of typical specimens of the foliage and firm-ripe fruit of the present variety of plum tree; such illustrations being of a twig with leaves, and separate fruit; one of the latter being cut in half to expose the flesh, with the stone remaining in one of the halves.

DESCRIPTION OF THE VARIETY

The botanical details of this new and distinct variety of plum tree—with color definitions (except those in common color terms) referenced to Reinhold Color Atlas by A. Kornerup and J. H. Wanscher—are as follows:

TREE

Size: Medium to large.
Vigor: Vigorous.
Growth: Upright.
Density: Medium.
Shape: Vase form.
Production: Productive.
Bearing: Regular.

TRUNK

Size: Medium stocky.
Texture: Shaggy.

BRANCHES

Size: Medium.
Texture: Rough to medium rough.
Color:
*New growth.*—Reddish brown.
*Old growth.*—Brown to grayish brown.

LEAVES

Size: Large. Average length — $3\frac{1}{2}''$ to $4\frac{3}{4}''$. Average width — $1\frac{1}{2}''$ to $1\frac{7}{8}''$.
Texture: Smooth.
Petiole:
*Average length.*—$\frac{1}{2}''$.
*Average width.*—1/16". Heavily grooved on upper longitudinal surface.
Glands:
*Average number.*—2. Usually positioned on base of leaf. Globose.
Color:
*Upper surface.*—Dark green (28-F-6 to 28-F-8).
*Lower surface.*—Dull green (27-E-3 to 27-E-4).
Margin: Serrate.
Shape: Primary. Many oblanceolate. Some elliptical.

FLOWER BUDS

Size: Medium.
Length: Medium to short.
Shape: Plump.

FLOWERS

Blooming period:
*Date of first bloom.*—Mar. 2, 1982.
*Date of full bloom.*—Mar. 7, 1982.
Color: White.
Size: Medium.

FRUIT

Maturity when described: Firm ripe.
Date of first picking: May 29, 1982.
Date of last picking: June 5, 1982.
Distribution on tree: Evenly.
Size: Medium
*Average diameter axially.*—$1\frac{1}{2}''$.
*Average transversely in suture plane.*—$2\frac{1}{4}$.
Form: Uniform. Somewhat oblate; i.e., flattened at stem and apex.
Suture: Shallow. Extends from apex to base.
Cavity: Rounded to slightly elongated in suture plane.
*Average depth.*—$\frac{3}{8}''$.
*Average breadth.*—$\frac{1}{2}''$.
Base: Retuse.
Apex: Rounded to slightly retuse.
Stem:
*Average length.*—$\frac{1}{2}''$.
*Average width.*—3/32".

SKIN

Thickness: Medium.
Texture: Medium.
Tenacity: Tenacious.
Tendency to crack: None.
Down: Wanting.
Color: Bordeaux red (11-D-8) to Garnet red (11-E-8).

FLESH

Ripens: Evenly.
Texture: Firm. Meaty.
Eating quality: Good.
Flavor: Mild. Subacid.
Color: Yellow (4-A-8 to 5-B-8).

STONE

Type: Clingstone.
Size: Small.
*Average length.*—$\frac{3}{4}''$.
*Average width.*—$\frac{3}{4}''$.
*Average thickness.*—5/16".
Color: Brownish orange (7-C-5 to 7-C-6).
Apex: Acuminate.
Base: Oblique.
Surface: Irregularly furrowed. Ridged near base.
Dorsal Edge: Broad grooved wing — usually near base.
Ventral edge: Thin.
Tendency to split: None.

USE

Local and long distance market.

KEEPING QUALITY

Good.

SHIPPING QUALITY

Good.

The plum tree and its fruit herein described may vary in slight detail due to climatic and soil conditions under which the variety may be grown; the present description being of the variety as grown in the Central Valley of California.

We claim:

1. A new and distinct variety of plum tree, substantially as illustrated and described, characterized by medium size, uniform, clingstone fruit having red skin, firm, yellow flesh, and good keeping, long distance shipping, and eating qualities; the fruit—evenly distributed throughout the tree—having the general shape of the Nubiana and ripening three days earlier than the Spring Beaut.

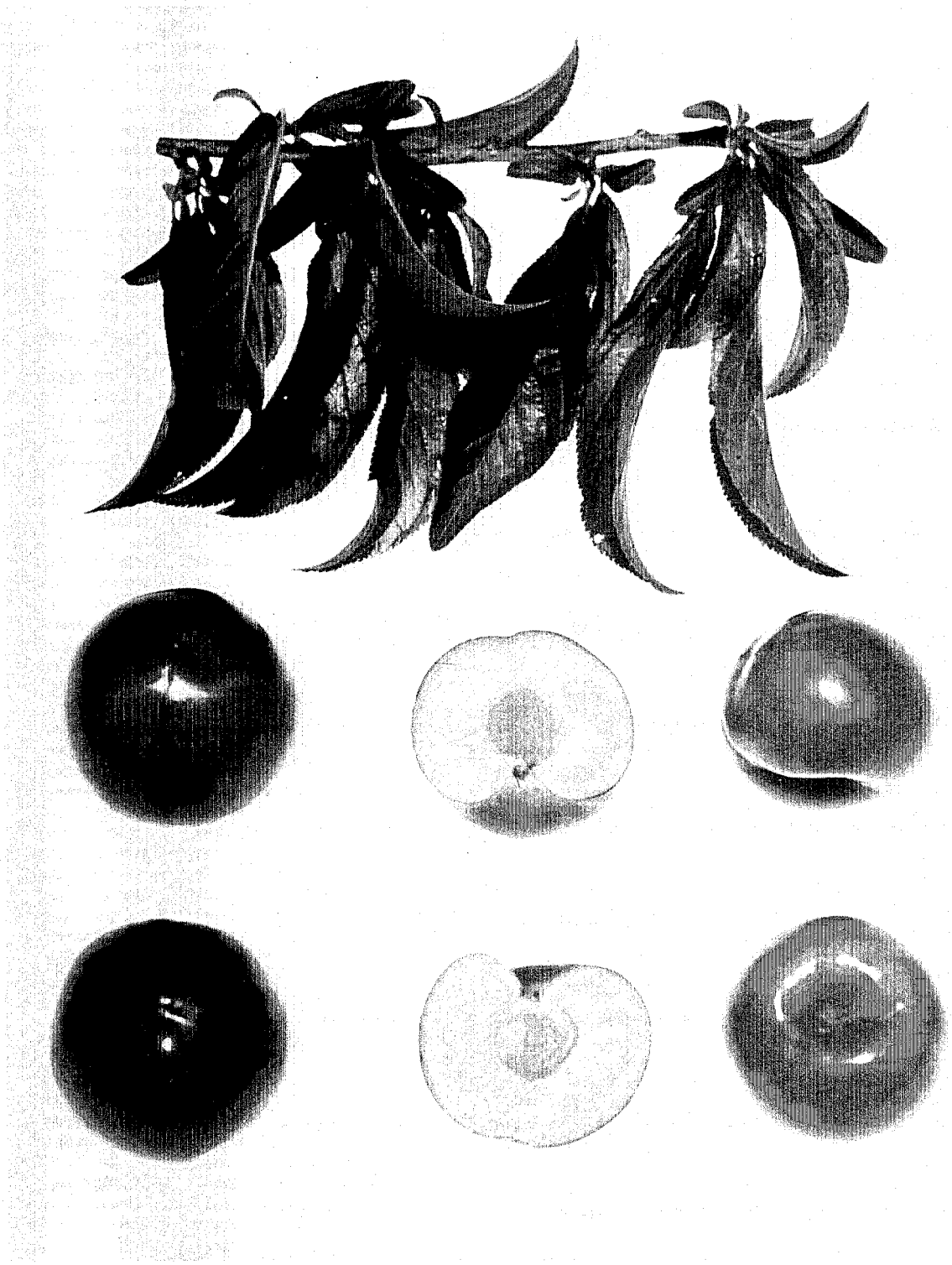

* * * * *